(12) United States Patent
Liu et al.

(10) Patent No.: US 7,205,701 B2
(45) Date of Patent: Apr. 17, 2007

(54) PASSIVE WIRELESS ACOUSTIC WAVE CHEMICAL SENSOR

(75) Inventors: James Liu, Rockford, IL (US); Peter P. Dierauer, Freeport, IL (US); Mark A. Repko, Freeport, IL (US)

(73) Assignee: Honeywell International Inc., Morristown, NJ (US)

( * ) Notice: Subject to any disclaimer, the term of this patent is extended or adjusted under 35 U.S.C. 154(b) by 134 days.

(21) Appl. No.: 10/933,945

(22) Filed: Sep. 3, 2004

(65) Prior Publication Data

US 2006/0049714 A1 Mar. 9, 2006

(51) Int. Cl.
*H01L 41/04* (2006.01)

(52) U.S. Cl. .................................. 310/313 R
(58) Field of Classification Search ............ 310/313 R, 310/313 B, 313 D, 338
See application file for complete search history.

(56) References Cited

U.S. PATENT DOCUMENTS

| | | | |
|---|---|---|---|
| 4,216,401 A | | 8/1980 | Wagner |
| 4,454,440 A | | 6/1984 | Cullen |
| 5,243,539 A | * | 9/1993 | Holt et al. ..................... 702/30 |
| 5,321,331 A | * | 6/1994 | Baer et al. .............. 310/313 D |
| 5,402,791 A | * | 4/1995 | Saitoh et al. ................ 600/459 |
| 5,471,723 A | | 12/1995 | Luder et al. |
| 5,551,953 A | | 9/1996 | Lattin et al. |
| 5,795,993 A | * | 8/1998 | Pfeifer et al. .............. 73/24.01 |
| 5,821,425 A | | 10/1998 | Mariani et al. |
| 6,067,474 A | | 5/2000 | Schulman et al. |
| 6,079,276 A | | 6/2000 | Frick et al. |
| 6,144,332 A | | 11/2000 | Reindl et al. |
| 6,350,609 B1 | | 2/2002 | Morozov et al. |
| 6,374,678 B1 | | 4/2002 | Masuda |
| 6,442,413 B1 | | 8/2002 | Silver |
| 6,484,585 B1 | | 11/2002 | Sittler et al. |
| 6,497,729 B1 | | 12/2002 | Moussy et al. |
| 6,514,689 B2 | | 2/2003 | Han et al. |
| 6,541,893 B2 | | 4/2003 | Zhu et al. |

(Continued)

FOREIGN PATENT DOCUMENTS

WO 0054042 9/2002

(Continued)

OTHER PUBLICATIONS

Pohl et al., "Monitoring the Tire Pressure at Cars Using Passive SAW Sensors," IEEE Ultrasonics Symposium, pp. 471-471, Oct. 1997.

(Continued)

*Primary Examiner*—Darren Schuberg
*Assistant Examiner*—Derek Rosenau
(74) *Attorney, Agent, or Firm*—Brian N. Tufte

(57) ABSTRACT

A passive wireless acoustic wave chemical sensor can be utilized for monitoring the concentration of an analyte in a substance such as blood. Such an acoustic wave chemical sensor can be configured to include one or more interdigital transducers and a selective coating formed upon a piezoelectric substrate. The coating and the interdigital transducer(s) can be used to convert electrical signal to surface waves thereof. An antenna can be connected to the acoustic wave device, wherein the antenna receives one or more input signals, which excite the acoustic device and to produce an output signal that is related to the concentration of the analyte of interest.

3 Claims, 6 Drawing Sheets

U.S. PATENT DOCUMENTS

| | | | |
|---|---|---|---|
| 6,546,268 | B1 | 4/2003 | Ishikawa et al. |
| 6,550,337 | B1 | 4/2003 | Wagner |
| 6,571,638 | B2 | 6/2003 | Hines et al. |
| 6,579,498 | B1 | 6/2003 | Eglise |
| 6,662,642 | B2 * | 12/2003 | Breed et al. ............... 73/146 |
| 6,872,786 | B2 * | 3/2005 | Murray et al. ........... 525/326.7 |
| 2002/0011366 | A1 | 1/2002 | Fuchs et al. |
| 2002/0024450 | A1 | 2/2002 | Townsend et al. |
| 2002/0026224 | A1 | 2/2002 | Thompson et al. |
| 2002/0078757 | A1 | 6/2002 | Hines et al. |
| 2002/0103425 | A1 | 8/2002 | Mault |
| 2002/0138009 | A1 | 9/2002 | Brockway et al. |
| 2002/0154029 | A1 | 10/2002 | Watters et al. |
| 2003/0042998 | A1 * | 3/2003 | Edmonson ................. 333/195 |
| 2003/0154031 | A1 | 8/2003 | Alexandrovich et al. |
| 2004/0244466 | A1 * | 12/2004 | Shen ........................ 73/24.01 |
| 2006/0032290 | A1 * | 2/2006 | Liu ........................... 73/29.02 |

FOREIGN PATENT DOCUMENTS

| | | |
|---|---|---|
| WO | WO 03/081195 | 10/2003 |

OTHER PUBLICATIONS http://www.devicelink.com/mem/archive/00/10/006.html, Implications of RIFCs for Medical Instrumentation, 11 pp., printed Feb. 6, 2004.

http:www.uchc.edu/ocomm/newsreleases01/june01/glucosesensor.html, Implantable Glucose Monitor for Diabetics, 2 pp., printed Feb. 6, 2004.

http://www.defeatdiabetes.org/Articles/biosensor030407.htm, Defeat Diabetes: Patent Issued for New Implantable Glucose Biosensor, 1 p., printed Feb. 6, 2004.

http//:www.ecs.soton.ac.uk/publications/rj/1994/transduc/white/white.html, A Thick Film Acoustic Wave Sensor, 6 pp., printed Mar. 5, 2004.

http://ww.sensorsmag.com/articles/1000/68/main.shtml, Sensors—Oct. 2000—Acoustic Wave Technology Sensors, 15 pp., printed Mar. 5, 2004.

http://www.devicelink.com/grabber.php3?URL=http://www.devicelink.com/mem/archive/..., 15 pp., printed Mar. 17, 2004.

http://afgen.com/controv7.html, The Mark of the New World Order: I.D. Biochip in your Right Hand!, 3 pp., printed Feb. 6, 2004.

http://www.advanced-polymers.com/star_center/technical_papers/reduction_in_effective_constant.pdf, 1 p., Honeywell, prior to filing date of the application.

Grimes et al., "Thin-Film Magnetoelastic Microsensors for Remote Query Biomedical Monitoring," Biomedical Microdevices, 2:1, pp. 51-60, 1999.

Honeywell International Inc., U.S. Appl. No. 10/828,142, filed Apr. 20, 2004, entitled, Pressure Sensor Methods and Systems.

Dai Enguang et al., "Passive and remote sensing based upon surface acoustic wave in special environments," SBMO/IEEE MTT-S IMOC 97 Proceedings, pp. 133-139, Aug. 1997.

Reindl et al., "SAW Devices as Wireless Passive Sensors," IEEE Ultrasonics Symposium, pp. 363-367, Nov. 1996.

* cited by examiner

Time

PASSIVE WIRELESS ACOUSTIC WAVE CHEMICAL SENSOR

TECHNICAL FIELD

The present invention generally relates to chemical and/or biochemical sensing devices, and more particularly, to acoustical wave chemical and/or biochemical sensing devices.

BACKGROUND

Surface acoustic wave sensors can be utilized in a wide variety of sensing applications, and can often provide a highly sensitive detection mechanism due to their high sensitivity to surface loading and low noise due to their intrinsically high Q factor. Surface acoustic wave devices are typically fabricated using photolithographic techniques with comb-like interdigital transducers placed on a piezoelectric material.

SUMMARY

The present invention relates to acoustical wave chemical and/or biochemical sensing devices, systems and methods. In one illustrative embodiment, a chemical sensor is provided that includes a surface acoustic wave device that has an absorbing layer along an acoustic path. The absorbing layer may be adapted to selectively absorb a chemical and/or biochemical constituent of interest, and may effect the mass loading along an acoustic path of the surface acoustic wave device. In some embodiments, the surface acoustic wave device may be in a delay line configuration, and the change in mass loading along the acoustic path may result in a delay time shift that corresponds to the concentration of the chemical and/or biochemical constituent of interest. In other embodiments, the surface acoustic wave device may be in a resonator configuration, and the change in mass loading along the acoustic path may result in a change in the resonant frequency, which corresponds to the concentration of the chemical and/or biochemical constituent of interest. In some cases, the surface acoustic wave device may be adapted to operate above 2.5 GHz, above 4.0 GHz, or above 5.0 GHz, if desired.

In some embodiments, the surface acoustic wave sensor may be a battery-less and wireless device. For example, the surface acoustic wave device may be configured to wirelessly receive a power signal that powers the surface acoustic wave device, and further configured to provide a wireless output signal. In some cases, a remote interrogator may be used to provide the wireless power signal and to receive the wireless output signal, as desired. A battery-less and wireless chemical sensor may be useful in a wide variety of applications. For example, such a device may be useful as an implantable device. For example, such a device may be implanted into a human body and used to monitor one or more chemical and/or biochemicals (such as glucose) within the body.

The surface acoustic wave sensor may have at least one interdigital transducer above a piezoelectric substrate. When the power signal is provided to an interdigital transducer, sometimes wirelessly through an antenna, an acoustic wave is produced in the piezoelectric substrate along the acoustic path. The absorbing layer or substance may be coupled to the piezoelectric substrate along at least part of the acoustic path. The absorbing layer or substance may be adapted to selectively absorb a chemical and/or biochemical constituent of interest, and may effect the mass loading along the acoustic path.

At least one of the interdigital transducers may receive the acoustic wave after passing along the acoustic path and the absorbing layer or substance, and in response, may produce an output signal that is related to the amount of chemical and/or biochemical absorbed by the absorbing layer or substance. In some cases, the output signal is transmitted to a remote interrogator, sometimes wirelessly through an antenna.

In some illustrative embodiments, one or more reflectors may be situated on the piezoelectric substrate, and may be used to reflect an acoustic wave back toward one or more interdigital transducers. For example, and in one illustrative embodiment, the same interdigital transducer may be used to generate an acoustic wave and to receive a reflected acoustic wave after traveling along the acoustic path. In some embodiments, the absorbing layer or substance is situated between an interdigital transducer and the one or more reflectors. For example, and in one illustrative embodiment, the surface acoustic wave device may include one or more first reflectors situated on one side of an interdigital transducer, and one or more second reflectors on an opposite side of the interdigital transducer. An absorbing layer may be situated between the interdigital transducer and the one or more first reflectors. The acoustic path between the interdigital transducer and the one or more first reflectors may be used to provide a measure of the concentration of the chemical and/or biochemical constituent of interest. The acoustic path between the interdigital transducer and the one or more second reflectors may be used as a baseline, or may be used to provide a measure of some other environmental parameter such as temperature, pressure or any other suitable parameter.

In some embodiments, the surface acoustic wave sensor may be capable of being excited in multiple modes, sometimes through an appropriate power signal. When so provided, the same surface acoustic wave sensor may be used to detect multiple parameters. For example, and when configured in a resonance configuration, multiple frequency shifts may be detected via multiple orthogonal modes of vibration, which can then be used to estimate multiple environmental parameters such as chemical concentration, temperature, pressure, etc.

In some cases, an affinity bond may arise between the chemical and/or biochemical constituent of interest and the absorbing layer or substance. It has been found that this can cause the chemical molecules that are to be sensed to remain on or near the top of the absorbing layer or substance, and slow down the response time of the sensor. In some illustrative embodiments, a higher-amplitude mode may initially be provided to break down the affinity bonds. Once the bonds are sufficiently broken down, a lower-amplitude mode may be used to measure the concentration of the chemical and/or biochemical constituent of interest. In some cases, the higher-amplitude mode may correspond to a shear-horizontal mode in the piezoelectric substrate, but this is not required in all embodiments.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE DRAWINGS

Figure 1:
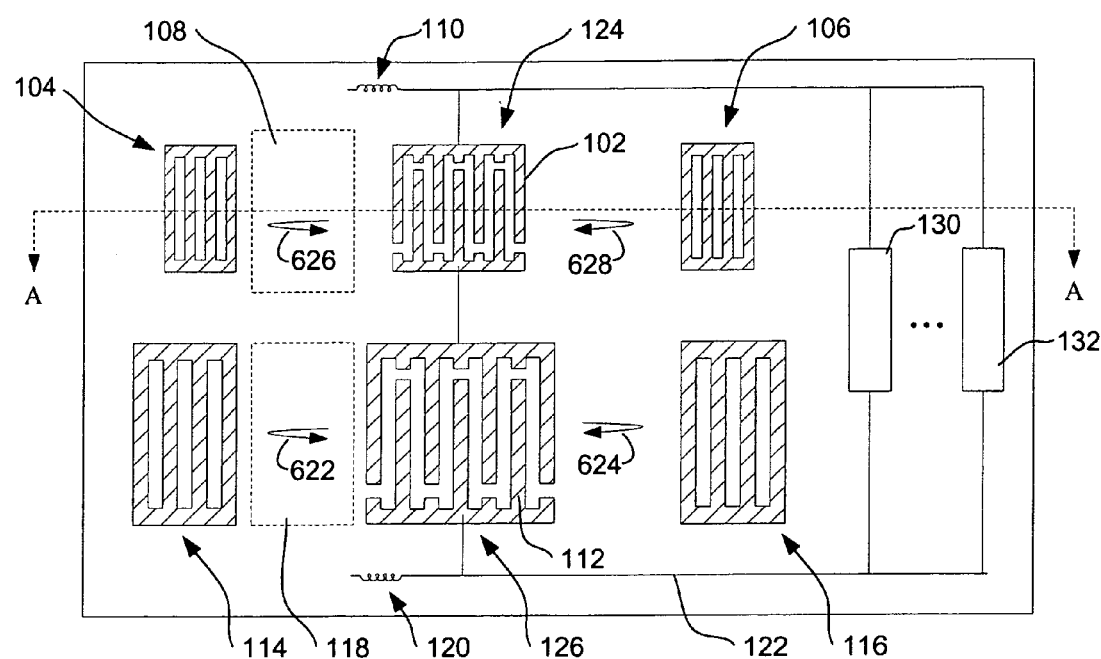
FIG. 1 is a schematic top view of a surface acoustic wave resonance sensor in accordance with one illustrative embodiment of the present invention.

FIG. 1 is a schematic top view of a surface acoustic wave resonance sensor in accordance with an illustrative embodiment of the present invention. The illustrative surface acoustic wave sensor of FIG. 1 is configured in a resonance configuration; that is, the output signal of the surface acoustic wave sensor will tend to be larger at one or more resonance frequencies, as further described below.

The illustrative surface acoustic wave sensor includes two interdigital transducers 102 and 112, although this is not required in all embodiments. In the illustrative embodiment, the interdigital transducers 102 and 112 are each adapted to produce a different acoustic wavelength. The acoustic wavelength is determined, at least in part, by the line width and spacing of the interdigital electrode fingers of each interdigital transducer 102 and 112. In each case, the interdigital electrodes may have a line width and/or spacing that is a multiple of about one quarter of the desired acoustic wavelength. In some cases, the interdigital transducer may be designed to operate with an acoustical frequency that is greater than 2.5 GHz, greater than 4.0 GHz, or even greater than 5 GHz, but this is not required.

As can be seen from FIG. 1, the line width and spacing of interdigital transducer 102 is less than the line width and spacing of interdigital transducer 112. Thus, the wavelength of the acoustic wave produced by interdigital transducer 102 may be less than the wavelength of the acoustic wave produced by interdigital transducer 112. The interdigital electrodes may be made from any suitable material such as aluminum (Al), platinum (Pt), gold (Au), rhodium (Rh), iridium (Ir), copper (Cu), titanium (Ti), tungsten (W), chromium (Cr), or nickel (Ni), etc.

In the illustrative embodiment, the interdigital transducers 102 and 112 are formed on a piezoelectric substrate 122. When an AC signal is applied to the interdigital transducers 102 and 112, an electric field is produced between the individual electrode fingers, and the piezoelectric effect of the piezoelectric substrate 122 causes a mechanical displacement that generates a surface acoustic wave in the piezoelectric substrate 122. The piezoelectric substrate 122 may be formed from any suitable piezoelectric material, including for example, quartz, polymeric piezoelectric materials, bio-inert ceramic materials such as Alumina, or any other suitable piezoelectric material, as desired.

A first antenna 110 may be coupled to a first set of fingers of the interdigital transducer 102. The first antenna 110 may be adapted to receive a wireless input signal, which in some cases, may be a wireless power signal. The wireless power signal may provide sufficient power to cause the interdigital transducer 102 to produce a surface acoustic wave in the piezoelectric substrate 122. A second set of fingers of interdigital transducer 102 may also be provided. The second set of fingers of interdigital transducer 102 may be electrically coupled to the first set of fingers via capacitive coupling. In the illustrative embodiment, the second set of fingers of interdigital transducer 102 are electrically coupled to a first set of fingers of the interdigital transducer 112 by a metal trace or other suitable connection. A second set of fingers of the interdigital transducer 112 are connected to a second antenna 120, as shown. The second antenna 120 may be adapted to provide an output signal, and in some cases, a wireless output signal, which can be read and processed by an interrogator. In some cases, the first antenna 110 and the second antenna 120 may be the same antenna, if desired.

During operation, a wireless power signal is directed at the first antenna 110. The input power signal received by the first antenna 110 is coupled to both the first interdigital transducer 102 and the second interdigital transducer 112. In response, the first interdigital transducer 102 produces a first surface acoustic wave in the piezoelectric substrate 122, and the second interdigital transducer 112 produces a second surface acoustic wave in the piezoelectric substrate 122.

In the illustrative embodiment, the first surface acoustic wave travels in both a leftward direction toward reflector 104 along an acoustic path, and in a rightward direction toward reflector 106 along an acoustic path. The acoustic wave engages both reflectors 104 and 106, and is reflected back to the first interdigital transducer 102. The first interdigital transducer 102 converts the reflected acoustic waves back into electrical signals, which are then passed to the second interdigital transducer 112 and eventually to the second antenna 120. Likewise, the second surface acoustic wave travels in both a leftward direction toward reflector 114 along an acoustic path, and in a rightward direction toward reflector 116 along an acoustic path. The acoustic wave engages both reflectors 114 and 116, and is reflected back to the second interdigital transducer 112. The second interdigital transducer 112 converts the reflected acoustic waves back into electrical signals, which are then passed to the second antenna 120.

In the illustrative embodiment, an absorbing layer or substance 108 is coupled to the piezoelectric substrate 122 along at least part of the acoustic path 626 between the first interdigital transducer 102 and the reflector 104. Likewise, an absorbing layer or substance 118 is coupled to the piezoelectric substrate 122 along at least part of the acoustic path 622 between the second interdigital transducer 112 and the reflector 114. The absorbing layer or substances 108 and 118 may be adapted to selectively absorb a chemical and/or biochemical constituent of interest, and may effect the mass loading along the acoustic paths 622 and 626.

The first interdigital transducer 102 may receive the acoustic wave after passing along the acoustic path 626 and the absorbing layer or substance 108, and in response, may produce an output signal that is related to the amount of chemical and/or biochemical absorbed by the absorbing layer or substance 108. In some cases, the acoustic path 628 between the interdigital transducer 102 and reflector 106 may be used to provide a measure of some other environmental parameter such as temperature, pressure or any other suitable parameter, if desired. In some cases, the output signal from the first interdigital transducer 102 is transmitted to a remote interrogator, sometimes wirelessly through the second antenna 120.

Likewise, the second interdigital transducer 112 may receive the acoustic wave after passing along the acoustic path 622 and the absorbing layer or substance 118, and in response, may produce an output signal that is related to the amount of chemical and/or biochemical absorbed by the absorbing layer or substance 118. In some cases, the acoustic path 624 between the interdigital transducer 112 and reflector 116 may be used to provide a measure of some other environmental parameter such as temperature, pressure or any other suitable parameter, if desired. In some cases, the output signal from the second interdigital transducer 112 is transmitted to a remote interrogator, sometimes wirelessly through the second antenna 120.

As can be seen from FIG. 1, the second interdigital transducer 112 may have different finger width and/or spacing, which may produce an acoustic wave with a different wavelength than the first interdigital transducer 102. While not required, providing two separate interdigital transducer 102 and 112, each adapted to operate at different acoustic wavelengths, may help provide two separate measurements of the concentration of chemical and/or biochemical absorbed by the absorbing layer or substance for increased accuracy and reliability. Also, having two or more separate acoustic wavelengths may increase the sensitivity and/or operating range of the sensor. Also, and in some cases, the concentration of the sensed chemical and/or biochemical can be determined by the difference in resonant frequency of the two waves, if desired.

In some embodiments, the surface acoustic wave sensor may be capable of being excited in multiple modes, sometimes through the application of an appropriate power signal. In some cases, this may help the sensor detect multiple parameters. For example, and when configured in a resonance configuration as shown in FIG. 1, multiple frequency shifts may be detected via multiple orthogonal modes of vibration in the piezoelectric substrate 122, which can then be used to estimate or determine multiple environmental parameters such as chemical concentration, temperature, pressure, etc.

In some cases, an affinity bond may arise between the chemical and/or biochemical constituent of interest and the absorbing layer or substance 108, 118. It has been found that this can cause the chemical molecules that are to be sensed to remain on or near the top of the absorbing layer or substance 108, 118, and slow down the response time of the sensor. In some illustrative embodiments, and as further described below with respect to FIG. 6 below, a higher-amplitude mode may initially be provided to break down the affinity bonds. Once the bonds are sufficiently broken down, a lower-amplitude mode may be used to measure the concentration of the chemical and/or biochemical constituent of interest. In some cases, the higher-amplitude mode may correspond to a shear-horizontal mode in the piezoelectric substrate 122, but this is not required in all embodiments.

It is also contemplated that additional SAW sensors may be provided on or along the piezoelectric substrate 122, sometimes in parallel with the chemical and/or biochemical SAW sensors 124 and 126. In FIG. 1, a number of other SAW sensors 130 and 132 are schematically shown, and are connected in parallel with the chemical and/or biochemical SAW sensors 124 and 126 between antennas 110 and 120. The additional SAW sensors 130 and 132 may be, for example, other SAW chemical and/or biochemical SAW sensors that are sensitive to the same or different chemical and/or biochemical constituents, SAW pressure sensors, SAW temperature sensors, and/or any other suitable sensor, as desired. In some cases, each of the SAW sensors, or group of SAW sensors, may be configured to operate at different frequencies. For example, a SAW pressure sensor may be configured to operate at 2.410 MHz, a SAW temperature sensor may be configured to operate at 2.430 MHz, a SAW chemical sensor may be configured to operate at 2.450 MHz, and a SAW biological sensor may be configured to operate at 2.470 MHz. These are just example frequencies, and it is contemplated that other frequencies may be used, depending on the application. When so provided, each sensor or group of sensors may be interrogated separately by directing a corresponding wireless power signal at the first antenna.

Figure 2:
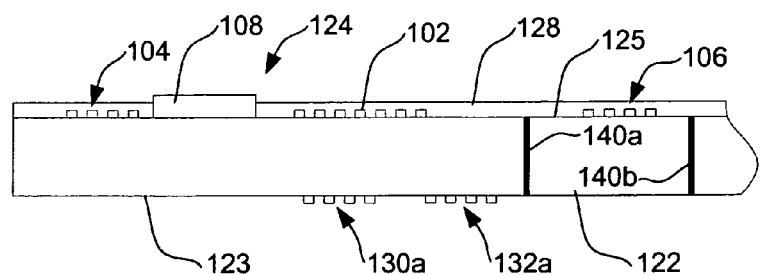
FIG. 2 is a cross-sectional side view of the illustrative embodiment of FIG. 1 taken along line A—A.

FIG. 2 is a cross-sectional side view of the illustrative embodiment of FIG. 1 taken along A—A. This diagram illustrates the interdigital transducer 102, reflectors 104 and 106, and chemical absorptive material substance 108 disposed on or above the piezoelectric substrate 122. The top of the surface acoustic wave device may be covered with a layer such as a non-thrombogenic agent 128, except for the chemical absorptive layer or substance 108. The non-thrombogenic agent 128 may help reduce thrombosis or similar ailments when the sensor is used for detecting chemical and/or biochemical constituent in blood.

Figure 4:
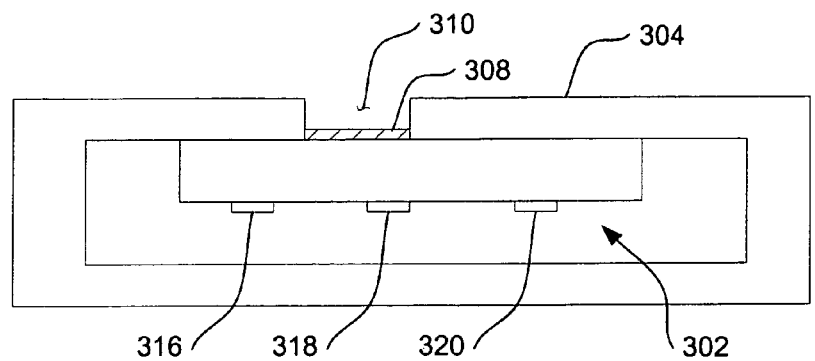
FIG. 4 is a schematic cross-sectional view of an illustrative surface acoustic wave sensor and package.

In some cases, additional SAW sensors may be provided on the same side 125 of the piezoelectric substrate 122 as the chemical and/or biochemical SAW sensors 124 and/or 126, and/or on the opposite or back side 123 of the piezoelectric substrate 122, as desired. For example, FIG. 2 shows that one or more SAW sensors, such as SAW sensor 130 of FIG. 1, may be provided on or along a back side 123 of the piezoelectric substrate 122, if desired. In one illustrative embodiment, the chemical and/or biochemical SAW sensors 124 and 126 are provided on a front side 125 of the piezoelectric substrate 122 with a corresponding absorbing layer or substance 108 and 118, respectively, exposed to a chemical and/or biochemical constituent of interest, and a pressure sensor 130a and/or temperature sensor 132a provided on the back side 123 of the piezoelectric substrate 122. In some cases, and as shown in FIG. 4, the sensors 316, 318 and 320 that are positioned on the back side 123 of the piezoelectric substrate 122 may be situated inside a package 304, as shown.

Referring back to FIG. 2, when there are sensors 130a and 130b positioned on the back side 123 of the piezoelectric substrate 122, one or more vias 140a and 140b may be provided through the piezoelectric substrate 122, as shown. These vias 140a and 140b may be used to electrically connect the sensors 130a and 130b to the antennas 110 and 120. As noted above, in some embodiments, the additional sensors 130a and 130b may be connected in parallel with the chemical and/or biochemical SAW sensors 124 and 126, and use the same antenna 110 and 120. However, this is not required, and it is contemplated that any suitable connection scheme may be used. Alternatively, or in addition, separate antenna may be provided on the back side 123 of the piezoelectric substrate 122, if desired. In some cases, the antenna 110 and 120 may be provided by some external device or devices such as a stent or any other suitable implantable conductive part, as desired.

Figure 3:
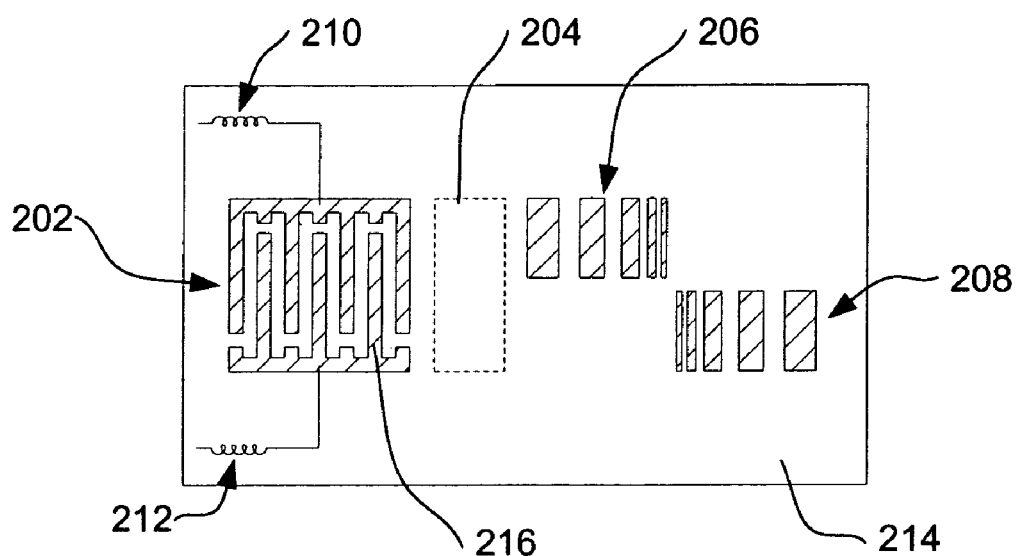
FIG. 3 is a schematic top view of a surface acoustic wave sensor in accordance with another illustrative embodiment of the present invention.

FIG. 3 is a schematic top view of a surface acoustic wave sensor 202 in accordance with another illustrative embodiment of the present invention. The illustrative surface acoustic wave (SAW) sensor 202 of FIG. 3 is configured in a delay line configuration; that is, the output signal of the surface acoustic wave sensor will be delayed relative to the input signal, as further described below.

In the illustrative embodiment, an interdigital transducer 216 may receive an input signal from a first antenna 210, and may generate a surface acoustic wave in the piezoelectric substrate 214. The acoustic wave may pass an absorbing layer or substance 204, which may be adapted to selectively absorb a chemical and/or biochemical constituent of interest, which may effect the mass loading along the acoustic path. In the illustrative embodiment, the acoustic wave is reflected back to the interdigital transducer 216 via reflectors 206 and 208. The output signal of the interdigital transducer 216 may then be provided to a second antenna 212. The antenna 212 may be adapted to wirelessly transmit the output signal to a remote interrogator (not shown).

Like above, two (or more) reflectors 206 and 208 may be provided. The parameters to measure in this embodiment are the delay times. Because of the mass loading effects of the absorbing layer or substance 204, the delay time is at least partially related to the amount of chemical and/or biochemical absorbed by the absorbing layer or substance 204. The delay time is also related to the spacing between the interdigital transducer 216 and the corresponding reflectors 206 and 208. Because two (or more) reflectors are provided, two (or more) separate measurements related to the amount of chemical and/or biochemical absorbed by the absorbing layer or substance 204 may be accomplished, which may result in increased accuracy and/or reliability. Also, having two or more separate delay times may increase the sensitivity and/or operating range of the sensor. In some cases, the concentration of the sensed chemical and/or biochemical can be determined by the difference in delay times for the two reflected waves, if desired.

FIG. 4 is a schematic cross-sectional view of an illustrative surface acoustic wave sensor and package. The illustrative surface acoustic wave sensor 302 is surrounded entirely by a package 304, except for an opening 310 that exposes the chemical absorption substance 308 to an analyte of interest. The sensor 302 is secured relative to the packaging 304 by an adhesive, solder, and/or any other suitable substance. The packaging 304 may be flat, cylindrical or have any other desired shape. The packaging 304 may include a bio-compatible material, since in some applications, the sensor may be implanted or otherwise used in conjunction with a living body.

Figure 5:
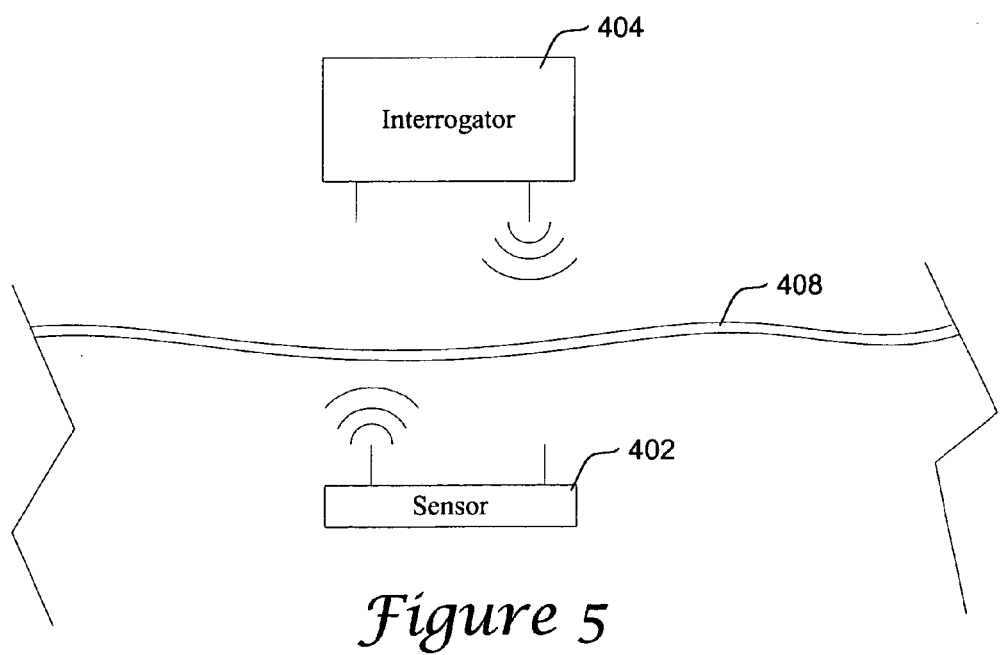
FIG. 5 is schematic diagram of an in-vivo application of the surface acoustic wave sensor of the present invention.

FIG. 5 is schematic diagram of an in-vivo application of the surface acoustic wave sensor of the present invention. In the illustrative embodiment, a surface acoustic wave sensor 402 is shown inserted under the skin 408 of a living human. A remote interrogator 404 is used to transmit and receive signals to/from the sensor 402. The interrogator 404 can be used to, for example, generate a number of input or power waveforms, which may be wirelessly transmitted to the surface acoustic wave sensor device 402. The input or power waveforms may be used to power up the surface acoustic wave sensor device 402. In response, the surface acoustic wave sensor device 402 may provide one or more output signals, which in some cases, are wirelessly received by the interrogator 404.

In some cases, and as noted above, the interrogator 404 may be adapted to excite multiple modes in the surface acoustic wave sensor device 402. In some cases, this may be accomplished by transmitting an appropriate input or power signal to the surface acoustic wave sensor device 402. In some cases, a surface acoustic wave mode (SAW), a pseudo surface acoustic wave mode (PSAW), and/or a leaky surface acoustic wave mode (LSAW) may be the easiest to excite, but others may also be excited if desired. The different excitation modes may be controlled by the interrogator 404 by providing input signals that have different frequency and/or power levels. For example, some excitation modes may have a higher impedance, and may require a higher power level to be excited.

In some cases, the surface acoustic wave sensor device 402 may be optimized so that some predetermined modes can be more easily excited, while suppressing other modes. This may be accomplished in any number of ways including, for example, selecting appropriate design parameters such as electrode thicknesses, finger widths and/or spacing of the interdigital transducer(s), the piezoelectric material used, the orientation of the interdigital transducer(s) relative to the crystalline planes in the piezoelectric material, etc.

Figure 6:
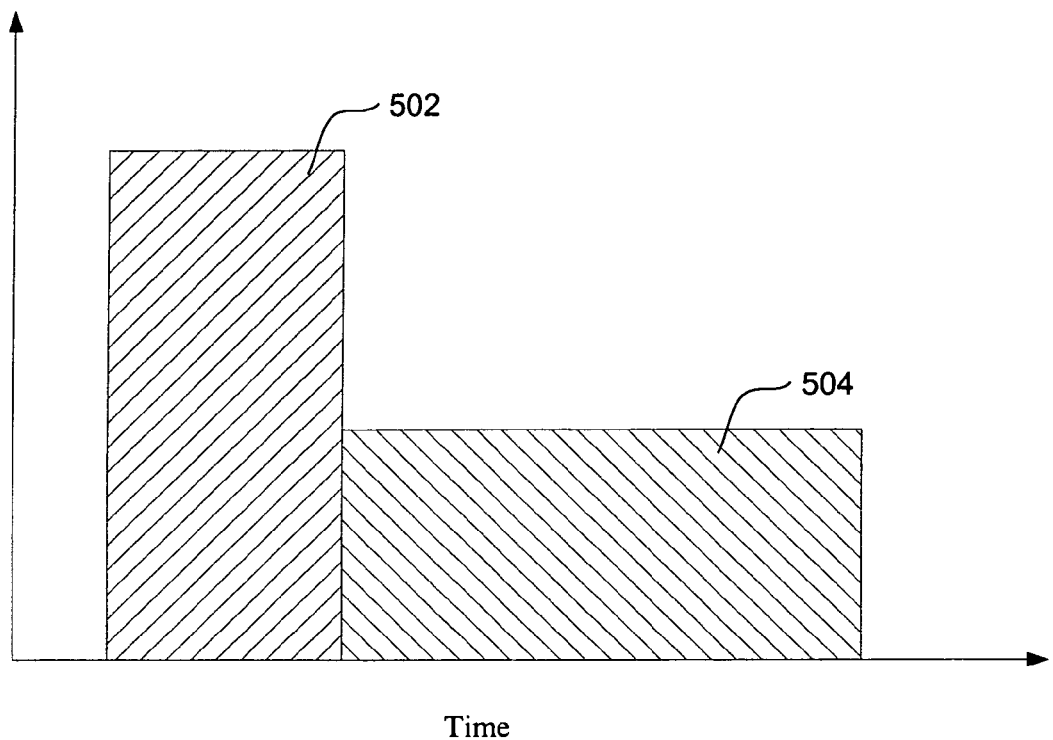
FIG. 6 is a graph showing an illustrative multiple mode startup sequence in accordance with the present invention.

FIG. 6 is a graph showing an illustrative multiple mode startup sequence in accordance with the present invention. Since sensor may be exposed to an analyte continuously, multiple modes 502 and 504 may be used to break down the bonds and/or desorb analyte in order to accurately measure the concentration of an analyte of interest. As noted above, in some cases, affinity bonds may arise between the chemical and/or biochemical constituent of interest and the absorbing layer or substance of the surface acoustic wave sensor device. It has been found that this can cause the chemical molecules that are to be sensed to remain on or near the top of the absorbing layer or substance, and slow the response time of the sensor.

As such, and in some illustrative embodiments, a first higher-amplitude mode 502 may be excited to help break down the affinity bonds. In some cases, a shear force may break the bonds more effectively than a normal direction force, and therefore, the higher-amplitude mode 502 may correspond to a shear-horizontal mode in the piezoelectric substrate, but this is not required in all embodiments. In some cases, overtones and/or other harmonics with increased frequencies and amplitudes may be employed. Usually, a higher amplitude vibration mode requires a higher drive level or current so that the combined effect of heat and mechanical vibration may help break down the bonds between the absorbing layer or substance and the analytes. Once the bonds are sufficiently broken down, a lower-amplitude mode 504 may be used to measure the concentration of the chemical and/or biochemical constituent of interest.

One or more higher-amplitude modes may also be used to help desorb the chemical and/or biochemical constituent of interest from the absorbing layer or substance. As noted above, a higher amplitude vibration mode may require a higher drive level or current. The effect of increased heat and/or mechanical vibration may help desorb the chemical and/or biochemical constituent of interest from the absorbing layer or substance, which may help prevent the absorbing layer or substance from becoming saturated. In some cases, a higher-amplitude mode 502 may be used to both break down affinity bonds as well as help desorb the chemical and/or biochemical constituent of interest from the absorbing layer or substance. In other cases, different higher-amplitude modes are used to break down affinity bonds and to desorb the chemical and/or biochemical constituent of interest from the absorbing layer or substance.

Figure 7:
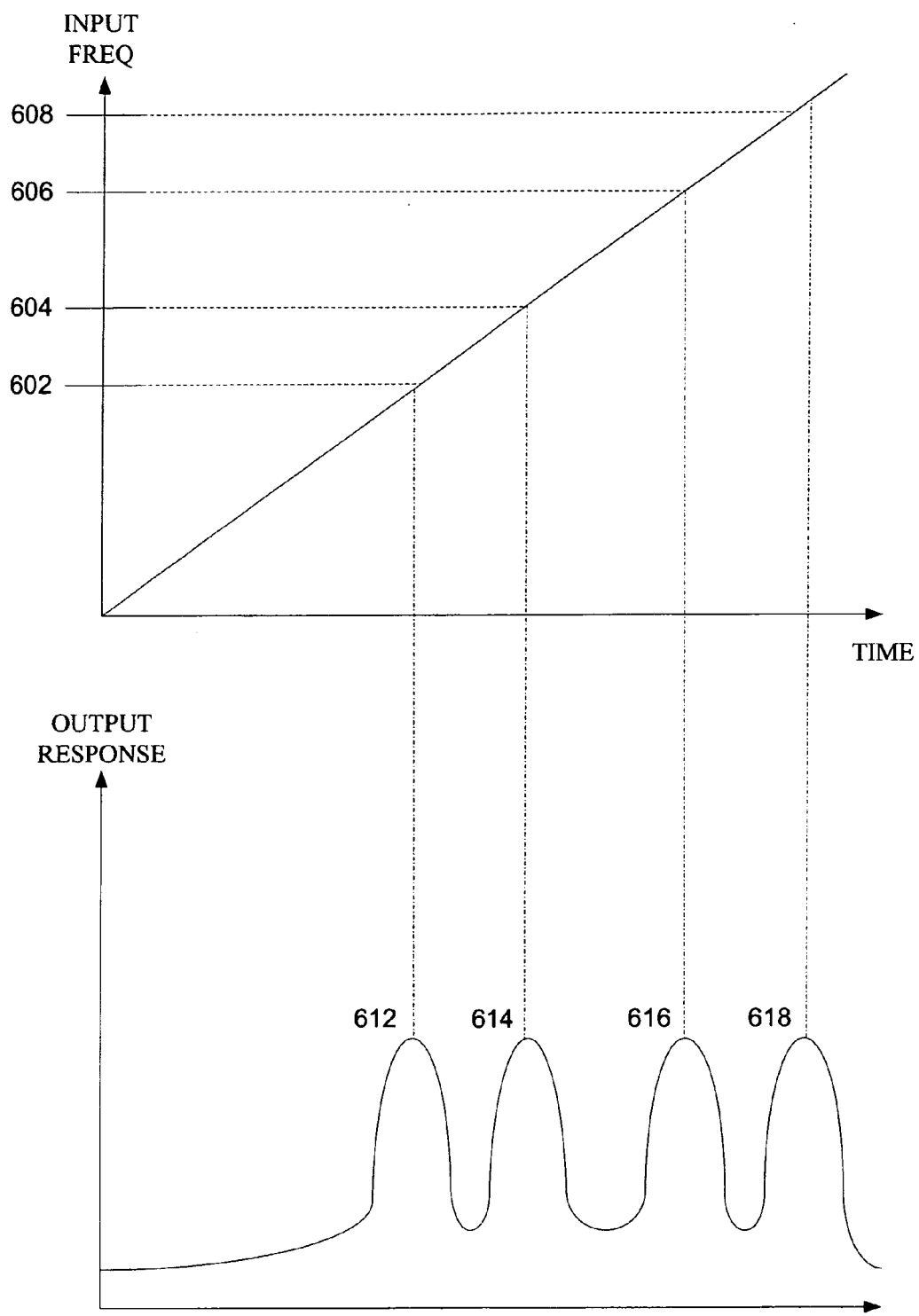
FIG. 7 is a graph showing an illustrative input and output signal for the surface acoustic wave resonance sensor of FIG. 1.

FIG. 7 is a graph showing an illustrative input and output signal for the surface acoustic wave resonance sensor of FIG. 1. In the illustrative graph, an input power signal is provided to the antenna 110 of FIG. 1. The input power signal is an AC power signal that includes an increasing frequency over time. As the frequency increases, there are four separate resonant frequencies that are eventually reached, noted as frequencies 602, 604, 606 and 608 in FIG. 7, corresponding with pulses 612, 614, 616, and 618. The first resonant frequency 602 corresponds to the acoustic wave that travels from the first interdigital transducer 102 to the reflector 106 and back, along acoustic path designated at 628 in FIG. 1. The second resonant frequency 604 corresponds to the acoustic wave that travels from the first interdigital transducer 102 to the reflector 104 and back, along acoustic path designated at 626 in FIG. 1. The third resonant frequency 606 corresponds to the acoustic wave that travels from the second interdigital transducer 112 to the reflector 116 and back, along acoustic path designated at 624 in FIG. 1. Finally, the fourth resonant frequency 608 corresponds to the acoustic wave that travels from the second interdigital transducer 112 to the reflector 114 and back, along acoustic path designated at 622 in FIG. 1.

The concentration of the chemical and/or biochemical absorbed by the absorbing layer or substance 108 may be determined by the second resonant frequency 604. Another measure of the concentration of the chemical and/or biochemical absorbed by the absorbing layer or substance 108 may be determined by the fourth resonant frequency 608. In some cases, the accuracy of the measurement can be verified by comparing the two concentrations. In some cases, the concentration of the chemical and/or biochemical absorbed by the absorbing layer or substance 108 may be determined by the difference between the first resonant frequency 604 and the second resonant frequency 604. The resonance frequencies 602 and 606 may be used as a baseline, or may be used to provide a measure of some other environmental parameter such as temperature, pressure or any other suitable parameter, as desired.

Figure 8:
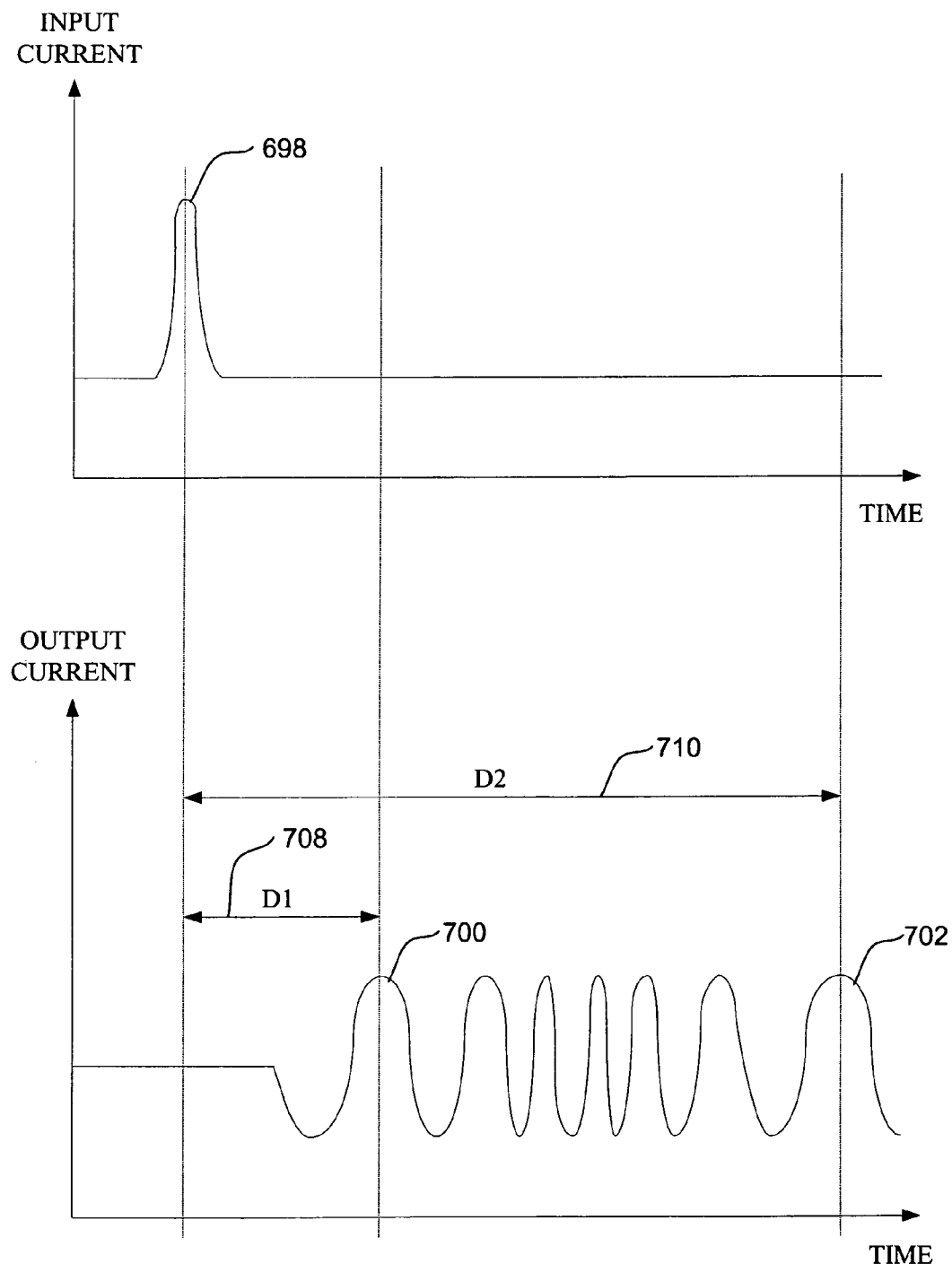
FIG. 8 is a graph showing an illustrative input and output signal of the surface acoustic wave delay line sensor of FIG. 3.

FIG. 8 is a graph showing an illustrative input and output signal of the surface acoustic wave delay line sensor of FIG. 3. In the illustrative graph, an input power signal pulse 698 is provided to the antenna 110 of FIG. 1. The input power signal pulse 698 causes the interdigital transducer 216 of FIG. 3 to produce an acoustic wave that propagates and reflects off of reflectors 206 and 208. The acoustic wave that is reflected by reflector 206 returns to the interdigital transducer 216, and causes a primary pulse 700 in the output signal, which is transmitted via antenna 212. The acoustic wave that is reflected by reflector 208 also returns to the interdigital transducer 216, and causes another primary pulse 702 in the output signal, which is also transmitted via antenna 212.

There is a first delay 708 between the input power pulse 698 and the first primary pulse 700. Likewise, there is a second delay 710 between the input power pulse 698 and the second primary pulse 702. The concentration of the chemical and/or biochemical absorbed by the absorbing layer or substance 204 may be determined by examining the first delay 708. As the absorbing layer or substance 204 absorbs more chemical and/or biochemical of interest, the mass loading along the acoustic path will increase, which will tend to increase the first delay 708. Another measure of the concentration of the chemical and/or biochemical absorbed by the absorbing layer or substance 204 may be determined by examining the second delay 710. In some cases, the accuracy of the measurement can be verified by comparing the two concentrations. In other cases, the concentration of the chemical and/or biochemical absorbed by the absorbing layer or substance 204 may be determined by the difference between the second delay 710 and the first delay 708.

Having thus described the preferred embodiments of the present invention, those of skill in the art will readily appreciated that the teachings found herein may be applied to yet other embodiments within the scope of the claims hereto attached.

What is claimed is:

1. A method for sensing a concentration of a chemical and/or biochemical constituent in a body fluid, the method comprising the steps of:

providing a surface acoustic wave device having an absorbing layer, wherein the absorbing layer absorbs the chemical and/or biochemical constituent and affects an output signal of the surface acoustic wave device dependent on the concentration of the chemical and/or biochemical constituent;

exposing the absorbing layer to the body fluid, thereby exposing the absorbing layer to the chemical and/or biochemical constituent;

wirelessly providing power to the surface acoustic wave device via a power signal;

wirelessly receiving the output signal from the surface acoustic wave device; wherein an altered output signal correlates to the concentration of the chemical and/or biochemical constituent in the body fluid; and wirelessly providing a desorb signal to the surface acoustic wave device, wherein the desorb signal causes the surface acoustic wave device to produce an acoustic wave that vibrates and causes heat in the absorbing layer, thereby causing the absorbing layer to desorb at least some of the absorbed chemical and/or biochemical constituent;

wherein the desorb signal has a different frequency than the power signal.

2. A method for sensing a concentration of a chemical and/or biochemical constituent in a body fluid, the method comprising the steps of:

providing a surface acoustic wave device having an absorbing layer, wherein the absorbing layer absorbs the chemical and/or biochemical constituent and affects an output signal of the surface acoustic wave device dependent on the concentration of the chemical and/or biochemical constituent in the body fluid;

exposing the absorbing layer to the chemical and/or biochemical constituent in the body fluid;

providing an initialization signal to the surface acoustic wave device, the initialization signal causing the surface acoustic wave device to produce an acoustic wave that helps break down bonds between the absorbing layer and the chemical and/or biochemical constituent to increase the response time of the surface acoustic wave device;

providing power to the surface acoustic wave device via a power signal; and receiving the output signal from the surface acoustic wave device, wherein the output signal is related to the concentration of the chemical and/or biochemical constituent;

wherein the initialization signal has a different frequency than the power signal.

3. A method for sensing a concentration of a chemical and/or biochemical constituent in a body fluid, the method comprising the steps of:

providing a surface acoustic wave device having an absorbing layer, wherein the absorbing layer absorbs the chemical and/or biochemical constituent and affects an output signal of the surface acoustic wave device dependent on the concentration of the chemical and/or biochemical constituent in the body fluid;

exposing the absorbing layer to the chemical and/or biochemical constituent in the body fluid;

providing an initialization signal to the surface acoustic wave device, the initialization signal causing the surface acoustic wave device to produce an acoustic wave that helps break down bonds between the absorbing layer and the chemical and/or biochemical constituent to increase the response time of the surface acoustic wave device;

providing power to the surface acoustic wave device via a power signal;

receiving the output signal from the surface acoustic wave device, wherein the output signal is related to the concentration of the chemical and/or biochemical constituent; and providing a desorb signal after the receiving step, wherein the desorb signal is of a higher amplitude than the power signal, and further has a different frequency than the power signal.

* * * * *